(12) United States Patent
Baratella (10) Patent No.: US 9,216,955 B2
(45) Date of Patent: Dec. 22, 2015

(54) POLYMORPHIC FORM OF FEXOFENADINE HYDROCHLORIDE, INTERMEDIATES AND PROCESS FOR ITS PREPARATION

(75) Inventor: Marco Baratella, Cerano (IT)

(73) Assignee: CHEMELECTIVA S.R.L., Novara (NO) (IT)

(*) Notice: Subject to any disclaimer, the term of this patent is extended or adjusted under 35 U.S.C. 154(b) by 255 days.

(21) Appl. No.: 13/697,861

(22) PCT Filed: Jun. 15, 2010

(86) PCT No.: PCT/IT2010/000268
§ 371 (c)(1),
(2), (4) Date: Nov. 14, 2012

(87) PCT Pub. No.: WO2011/158262
PCT Pub. Date: Dec. 22, 2011

(65) Prior Publication Data
US 2013/0059886 A1    Mar. 7, 2013

(51) Int. Cl.
*C07D 211/22*    (2006.01)

(52) U.S. Cl.
CPC .................... *C07D 211/22* (2013.01)

(58) Field of Classification Search
CPC .................................................. C07D 211/22
USPC ................................................. 546/239, 240
See application file for complete search history.

(56) References Cited

U.S. PATENT DOCUMENTS 7,470,789 B2 * 12/2008 Rao et al. .......... 546/239
8,236,961 B2 * 8/2012 Scubla et al. ...... 546/239

FOREIGN PATENT DOCUMENTS

| EP | 1260505 A1 | 11/2002 |
| WO | 2005/102999 A2 | 11/2005 |
| WO | 2009/034582 A2 | 3/2009 |

OTHER PUBLICATIONS

Side-by-Side, exhibit I, p. 1 (2014).*
Braga et al. "Crystal polymorphism . . . " Struct Bond, p. 25-50 (2009).*

* cited by examiner

*Primary Examiner* — Celia Chang
(74) *Attorney, Agent, or Firm* — Lucas & Mercanti, LLP (57) ABSTRACT

The present invention relates to a novel polymorphic form of Fexofenadine hydrochloride, to a process for preparing it, to pharmaceutical compositions containing it, as well as its use. The invention also relates to intermediates useful for the preparation of Fexofenadine hydrochloride, antihistamine drug used in the treatment of allergy symptoms.

13 Claims, 4 Drawing Sheets

XRPD pattern of polymorph φ of Fexofenadine hydrochloride

Figure 1: XRPD pattern of polymorph φ of Fexofenadine hydrochloride

Figure 2: DSC thermògram of polymorph φ of Fexofenadine hydrochloride

Figure 3: XRPD pattern of oxalic salt of formula (II)

Figure 4: XRPD pattern of the ketone of formula (V)

POLYMORPHIC FORM OF FEXOFENADINE HYDROCHLORIDE, INTERMEDIATES AND PROCESS FOR ITS PREPARATION

CROSS-REFERENCE TO RELATED APPLICATION

This application is a 371 of PCT/IT2010/000268, filed Jun. 15, 2010, the contents of which are incorporated herein by reference.

FIELD OF THE INVENTION

The present invention relates to a novel polymorphic form of Fexofenadine hydrochloride, to a process for preparing it, to pharmaceutical compositions containing it, as well as its use. The invention also relates to intermediates useful for the preparation of Fexofenadine hydrochloride, antihistamine drug used in the treatment of allergy symptoms.

BACKGROUND OF THE INVENTION

Fexofenadine is a second-generation antihistamine drug, without side effects, used in the treatment of allergy symptoms, related to histamine release. Histamine is a mediator of inflammation, antigen response and cellular injury, derived from the decarboxylation of the histidine, by the enzyme L-histidine decarboxylase. Histamine antagonists block release of histamine through inhibition of $H_1$ histamine receptors, especially found on skin, bronchus. The contact of an allergen (a substance that triggers an allergic reaction) with $H_1$ histamine receptors, causes the histamine release, that produce increased capillary permeability, vasodilation, consequently local erythemas, edemas (swellings) and rash. Furthermore, the release of histamine may induce itch, bronchospasm, gastrointestinal motility and secretion of salivary and bronchial glands.

Fexofenadine is the carboxylic acid derivative of Terfenadine of whom is the major metabolite, but without the cardiac toxicity than its parent compound. Fexofenadine does not cross the blood-brain barrier and no sedative or other central nervous system effects were observed. Fexofenadine hydrochloride is a compound of Formula (I)

(I)

2-[4-[1-hydroxy-4-[4-(hydroxydiphenylmethyl)-1-piperidyl]-butyl]phenyl]-2-methylpropanoic acid, which is disclosed in U.S. Pat. No. 4,254,129 and marketed under the trade name of Allegra®. Polymorphism is the property of some molecules and molecular complexes to assume more than one crystalline or amorphous form in the solid state. Substances are known which only appear in a single crystal or amorphous form; in addition, however, there are also substances which can form two, three or even more polymorphic crystal modifications. Polymorphs are distinct solids sharing the same molecular formula, having distinct advantageous and/or disadvantageous physical properties compared to other forms in the polymorph family.

The morphology of organo-chemical active substances is of great importance to the chemical and pharmaceutical development thereof. One crystalline form may have important advantageous properties compared to other crystalline forms. A process suitable for the synthesis of one crystalline form may offers different advantages to the API (Active Pharmaceutical Ingredients) producers, such as minimum number of chemical steps, the appropriate use of greener solvents and reagents, compounds with a high yield and purity The relevant polymorphism of an organo-chemical substance is always unpredictable in respect of the number of crystal modifications, the stability thereof and their behaviour in a living organism. The different polymorphs of a substance possess different energies of the crystal lattice and, thus, they show different physical properties of the solid state such as form, density, melting point, colour, stability, dissolution rate, milling facility, granulation, compacting etc. These differences in morphology and polymorphism may have drastic effects on the flowability of the milled solid (flowability affects the ease with which the material is handled during processing into a pharmaceutical product), development, transport stability and storage stability of individual administration forms, on the ability to produce different administration forms, on their application, on the solubility in polar or non-polar, protic or aprotic solvents, on solubility in aqueous solution, on solubility in the gastric juices, on solubility in blood serum, and finally on bio-availability. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. Other important properties of polymorphic forms relate to the ease of processing the form into pharmaceutical dosages, as the tendency of a powdered or granulated form to flow and the surface properties that determine whether crystals of the form will adhere to each other when compacted into a tablet. The polymorphic form may give rise to thermal behavior different from that of the amorphous material or another polymorphic form. Thermal behavior is measured in the laboratory by such techniques as capillary melting point, Differential Scanning calorimetry (DSC) and can be used to distinguish some polymorphic forms from others. A particular polymorphic form may also give rise to distinct spectroscopic properties that may be detectable by X-Ray Powder Diffraction (XRPD).

The same also applies in respect of the physical and chemical properties of Fexofenadine hydrochloride. It has been found that Fexofenadine hydrochloride may exist in various polymorphs.

WO 00/71124 discloses an amorphous form of Fexofenadine hydrochloride.

WO 95/31437 discloses anhydrous polymorphic forms (forms I and III) and hydrates polymorphic forms (forms II and IV) of Fexofenadine hydrochloride.

EP 1414453 dikloses a polymorph of Fexofenadine hydrochloride.

WO 2005102999 provides crystalline forms of Fexofenadine hydrochloride with different water content (4.4, 7.1 and 8%).

EP 1614681 reports a polymorph of Fexofenadine hydrochloride with a water content of 4.1%, that results difficult to be filter or to separate from the reaction or the crystallization medium.

U.S. Pat. No. 4,254,129 describes a synthesis of Fexofenadine by Friedel-Crafts acylation of an alkyl ester of α,α-dimethylbenzeneacetic acid with 4-halogenbutyryl chloride to give alkyl 4-(4-halogen-1-oxobutyl)-α,α-dimethylphenylacetate, that by reaction with α,α-diphenyl-4-piperidinemethanol, subsequently reduction of the cheto to the hydroxy compound and final hydrolysis of the ester group gave the Fexofenadine.

U.S. Pat. No. 6,815,549 describes a process to obtain Fexofenadine, by hydration of 4-{[4-(4-hydroxydiphenylmethyl)-1-piperidinyl]-1-butynyl}-α,α-dimethylbenzeneacetic acid and subsequently reduction.

The discovery of novel polymorphic forms of a pharmaceutically useful compound provides a new opportunity to improve the performance characteristics of a pharmaceutical product. It enlarges the repertoire of materials that a formulation scientist has available for designing a pharmaceutical dosage form, or a drug with a targeted release profile, or other desired characteristics, such as flowability and suitable rate of dissolution in aqueous fluid.

Most of the polymorphic forms of Fexofenadine hydrochloride until now known are extremely hygroscopic and/or deliquescent. They absorb water from the moisture already during the operation of separation from the reaction or the crystallization medium, when discharging the filter and/or the dryer. Moreover they may undergo a dissolution/reprecipitation in the moisture, resulting in a change of crystalline phase. This results in extreme technical problems of further processing the Fexofenadine hydrochloride, e.g., in order to produce pharmaceutical compositions. To enable production, usually high technical efforts have to be made and expensive equipment is necessary, like air conditioning to low relative moisture.

Therefore, the preparation of novel stable crystalline forms of Fexofenadine hydrochloride is desirable.

An object of the present invention is to provide a novel crystalline form of Fexofenadine hydrochloride, stable and easily to formulate, an economic and easy process, with few steps for preparing it, pharmaceutical compositions containing it, as well as its use.

SUMMARY OF THE INVENTION

Surprisingly, we have now found a novel polymorphic form of Fexofenadine hydrochloride defined as polymorph φ that is stable, not hygroscopic, not deliquescent, that can be stored, easy to handle, useful to produce stable pharmaceutical compositions.

Figure 2:
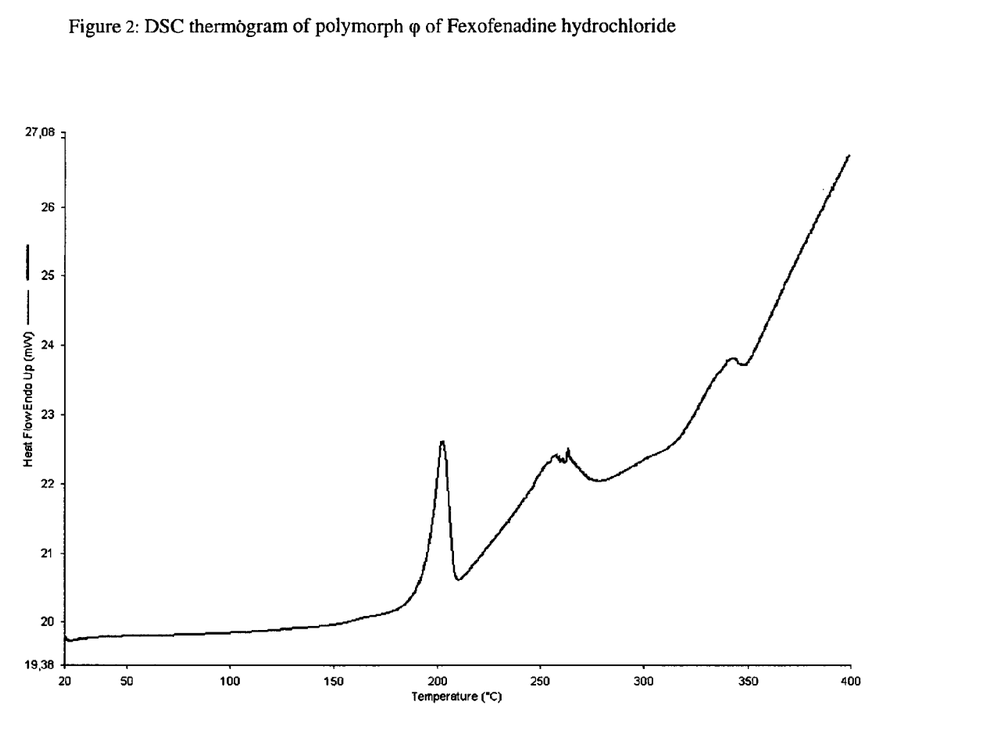
FIG. 2 provides a DSC thermogram of polymorph φ of Fexofenadine hydrochloride

The present invention provides a polymorph φ of Fexofenadine hydrochloride having a water content comprised between 3.2 and 3.4%±0.1% having an XRPD comprising peaks at 4.9, 9.9, 13.6, 15.8, 16.7, 18.1, 18.6, 19.9±0.2° 2θ and a DSC in accordance with FIG. 2.

In another embodiment, the invention provides a process for producing the polymorph φ of Fexofenadine hydrochloride according to claim 1, which comprises salifying a compound of formula (VI)

with hydrochloric acid in an ester as a solvent.

In another embodiment, the invention provides the use of polymorph φ of Fexofenadine hydrochloride for preparing a medicament.

In another embodiment, the invention provides a pharmaceutical composition comprising the polymorph φ of Fexofenadine hydrochloride.

In another embodiment, the invention provides a method of using the polymorph φ of Fexofenadine hydrochloride comprising administering the polymorph to a patient in need thereof.

The present invention also provides new synthetic intermediates useful for preparing Fexofenadine hydrochloride.

In another embodiment, the invention provides a compound of formula (II)

wherein R is is a $C_1$-$C_6$ alkyl.

Figure 4:
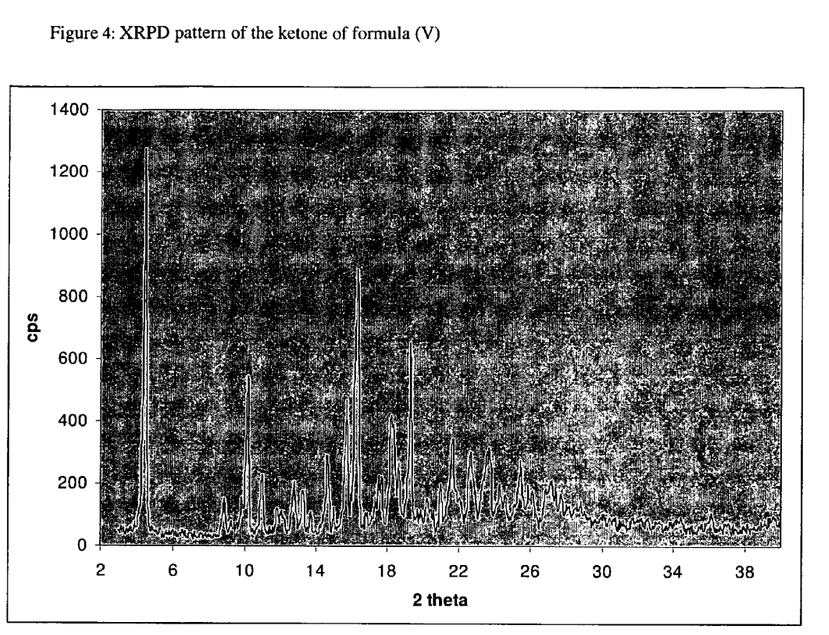
FIG. 4 provides an XRPD pattern of the ketone of formula (V).

In another embodiment, the invention provides a compound of formula (V)

characterized by a XRPD comprising peaks at 4.4, 10.2, 15.7, 16.3, 18.3, 19.3±0.2° 2θ; in accordance with FIG. 4.

In another embodiment, the invention provides use of compounds of formula (II) and (V) to prepare Fexofenadine hydrochloride.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

The terms "alkyl", "C1-C6 alkyl" refer, unless otherwise provided, to any straight or branched hydrocarbon having from 1 to 6 carbon atoms. Examples of alkyl groups include, without limitation, methyl, ethyl, n-propyl, isopropyl, n-butyl, sec-butyl, isobutyl, tert-butyl, n-pentyl, n-hexyl groups and the like. A preferred alkyl group of the present invention is methyl, ethyl.

The term "one pot" refers to a series of consecutive reactions that are carried out without removing any intermediate products.

The term "apolar solvent" refers to a solvent which is relatively inert to proton activity, i.e., not acting as a proton donor. Examples include, but are not limited to, hydrocarbons, such as pentane, hexane, heptane, cyclopentane, cyclohexane, and isomers thereof; aromatic solvents, such as benzene, toluene, o-, m- or p-xylenes; halogenated hydrocarbons, such as dichloromethane, chloroform; heterocyclic compounds, such as tetrahydrofuran, N-methylpyrrolidone; ethers, such as diethyl ether, dioxane, methyl terbutyl ether; and the like. The term "polar solvent" refers to a solvent that tends to provide protons. Examples of polar solvents include, without limitation, alcohols, such as methanol, ethanol, propanol, isopropanol, butanol, tert-butanol; or a solvent polarized due to the presence of an electron withdrawing group, for instance, esters, such as ethyl acetate, butyl acetate; nitriles, such as acetonitrile; ethers, such as diethyl ether; and the like.

These solvents are well known to a person skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example, or for environmental or toxicological reasons. Further discussions of polar or non-polar solvents may be found in organic chemistry textbooks or in specialized monographs, for example: *Organic Solvents Physical Properties and Method of Purification.* 4th ea., edited by John A. Riddick, et al., Vol. II, in the Techniques of Chemistry Series, John Wiley & Sons, New York, 1986.

The term "about" encompasses the range of experimental error that may typically occurs in a measurement (±5% of a value).

The process of the present invention is outlined in the Scheme 1 below, wherein the polymorph φ of Fexofenadine hydrochloride is obtained by salification of the compound of formula (VI), prepared by a process which comprises hydrolyzing the oxalic acid of a compound of formula (II), in presence of a base, to give a compound of formula (III); hydrating a compound of formula (III) in acid and optionally in the presence of a catalyst, to give a compound of formula (IV); hydrolyzing a compound of formula (IV) to give a compound of formula (V); reducing a ketone of formula (V) into the hydroxy compound of formula (VI) with a reducing agent.

Scheme 1.

The polymorph φ of Fexofenadine hydrochloride is obtained by salification of the compound of formula (VI) with hydrochloric acid, to give the corresponding hydrochloride salt in an ester, such as ethyl acetate, isopropil acetate, butyl acetate, preferably, ethyl acetate. The salification may be performed at a temperature ranging from 20° C. and 60° C., preferably at 40° C. In a preferred embodiment, the polymorph φ of Fexofenadine hydrochloride is obtained by salification of the compound of formula (VI) with 36% aqueous hydrochloric acid in ethyl acetate at 40° C.

The polymorph φ of Fexofenadine hydrochloride is easily filterable from the reaction or from the crystallization medium; can be easily washed with a suitable solvent, for instance ethylacetate, to remove any residual impurities and may be dried very fast at 50° C. under vacuum for few hours. This polymorph φ is stable, not hygroscopic, not deliquescent and shows good flowability properties. It does not absorb water after extended exposure at least for one year at room temperature with relative humidity of 60-70%. It is easy to handle and can be stored for a long period of time under normal storage conditions, to provide an industrial advantage for the production control and in order to produce pharmaceutical compositions.

Figure 1:
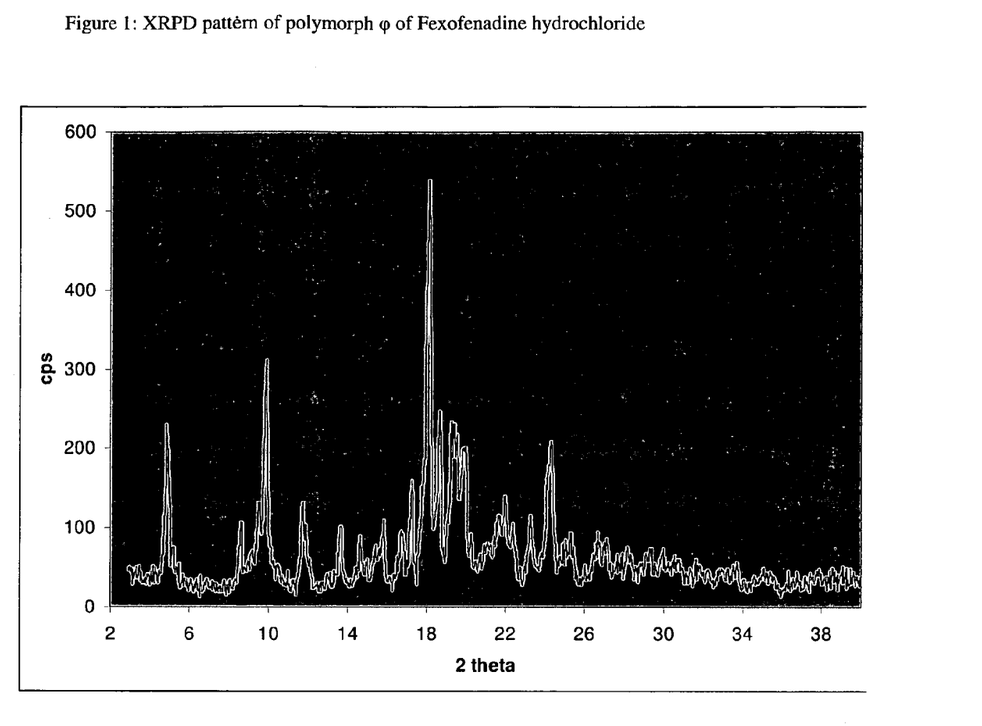
FIG. 1 provides an XRPD pattern of polymorph φ of Fexofenadine hydrochloride

In another embodiment, the invention provides the polymorph φ of Fexofenadine hydrochloride having a water content comprised between 3.2 and 3.4% ±0.1%; having an XRPD in accordance with FIG. 1 and a DSC in accordance with FIG. 2. The XRPD of the polymorph φ of Fexofenadine hydrochloride comprises peaks at 4.9, 9.9, 13.6, 15.8, 16.7, 18.1, 18.6, 19.9±0.2° 2θ.

The compound of formula (VI) is obtained by reduction of compound of formula (V) with a reducing agent. Any reducing agent well known to a person skilled in the art is a suitable reducing agent of the invention, for instance, hydrides, such as lithium aluminium hydride, diisobutylaluminium hydride; borohydrides, such as sodium, lithium, potassium borohydride. Preferably, the reducing agent is borohydride, more preferably sodium borohydride, in an aqueous mixture containing a polar solvent, preferably alcohol, such as methanol, ethanol. The reduction may be performed at a temperature ranging from room temperature to reflux temperature, preferably between room temperature and 60° C.

The compound of formula (V) is obtained by:
a) hydrating a compound of formula (III), (III)

wherein R is a C1-C6 alkyl, preferably methyl or ethyl, in acid and optionally in the presence of a catalyst, to give a compound of formula (IV), (IV)

wherein R is as defined above;
b) hydrolyzing a compound of formula (IV) to give a compound of formula (V) in presence of a base.

The hydration of a compound of formula (III), step a), occurs in the presence of an acid, for instance in aqueous solutions of strong acids, such as hydrochloric acid or sulfuric acid, preferably in an aqueous solution of sulfuric acid, in a suitable solvent, for instance, a polar solvent, such as an alcohol, for instance methanol, ethanol, isopropanol, preferably, methanol; and optionally in the presence of a catalyst, as described in *J. Org. Chem.* 1994, 59, 2620. A preferred catalyst of the present invention is mercury oxide. The hydration may be performed at a temperature ranging from room temperature to reflux temperature, preferably between room temperature and 60° C.

Any base well known to a person skilled in the art is a suitable base to hydrolyze a compound of formula (IV), step b). Inorganic or organic bases may be used. A preferred base is an inorganic base, such as sodium or potassium hydroxide, sodium or potassium carbonate, preferably sodium hydroxide.

Preferably, steps a) and b) are conducted in "one pot". Preferably, the intermediate of formula (IV) are not isolated and the mixture of the hydration reaction is directly hydrolyzed in a polar solvent, preferably an alcohol, for instance methanol, ethanol, isopropanol or a mixture of them in water, to give a compound of formula (V). The compound of formula (V) is in a crystalline form characterized by an XRPD, depicted in FIG. 4.

In another embodiment, the invention provides a compound of formula (V) characterized by a XRPD comprising peaks at 4.4, 10.2, 15.7, 16.3, 18.3, 19.3±0.2° 2θ.

The compound of formula (III) is obtained by hydrolysis of the salt of formula (II), in presence of a base. Any base well known to a person skilled in the art is a suitable base to hydrolyze the salt of formula (II). An inorganic base may be used, for instance, sodium or potassium hydroxide, sodium or potassium carbonate; or an organic base may be used, for instance, ammonia or amines, such as triethylamine, diisopropylamine. Preferably, the base is potassium carbonate, ammonia. Any solvent well known to a person skilled in the art is a suitable solvent. The solvent may be a polar or an apolar solvent, optionally in mixture with water. Preferably, the solvent is a mixture of toluene and water.

The salt of formula (II) is a novel compound, obtained by salification of the methyl 2-(4-(4-(4-(hydroxydiphenylmethyl)piperidin-1-yl)but-1-ynyl)phenyl)-2-methylpropionate, obtained as described in J. Org. Chem., Vol. 59, No. 9, 1994, 2621, with oxalic acid. Any solvent well known to a person skilled in the art is a suitable solvent. Preferably, the reaction is conducted in a polar solvent, for instance, an alcohol, such as methanol, ethanol, isopropanol; preferably, isopropanol. The salification is performed at a temperature ranging from room temperature to reflux temperature.

Figure 3:
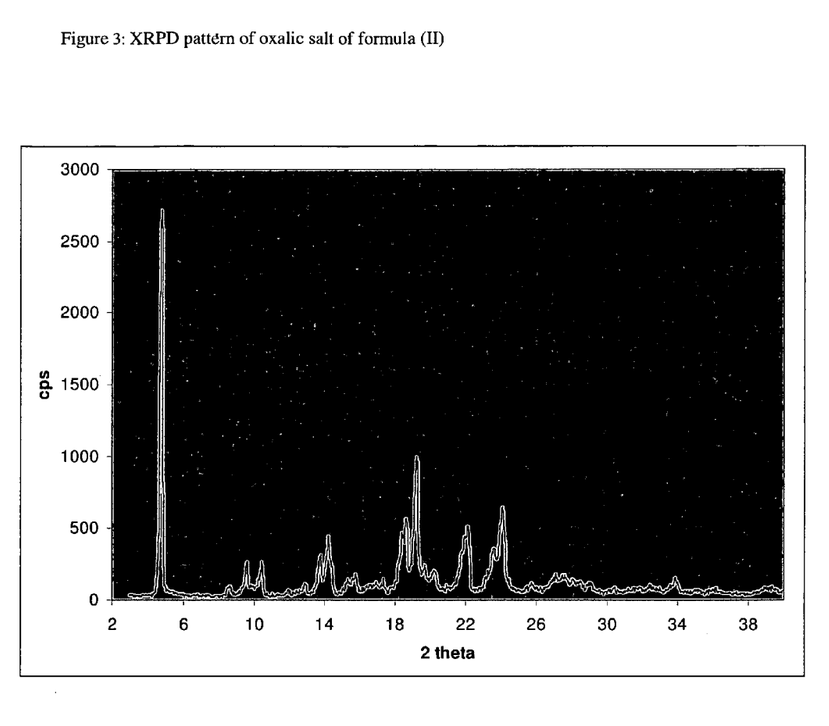
FIG. 3 provides an XRPD pattern of oxalic salt of formula (II).

In another embodiment, the invention provides a compound of formula (II), characterized by an XRPD, depicted in FIG. 3. The XRPD of the compound of formula (II) comprises peaks at 4.8, 9.6, 13.7, 14.2, 18.6, 19.2, 22.1±0.2° 2θ.

The process of the present invention to obtain the polymorph φ of Fexofenadine hydrochloride is a simple, efficient, high yields and economic process, particularly suited to large-scale preparation. The not hygroscopic polymorph φ of Fexofenadine hydrochloride is very useful to produce pharmaceutical compositions stable to moisture. It can be formulated and used as antihistaminic, antiallergic, broncodilatator.

Further object of the present invention is represented by the use of polymorph φ of Fexofenadine hydrochloride for the preparation of a medicament.

Further object of the present invention is a pharmaceutical composition comprising the polymorph φ of Fexofenadine hydrochloride in combination with one or several pharmaceutically acceptable excipients. A person skilled in the art is aware of a whole variety of such excipients suitable to formulate a pharmaceutical composition. Excipients include, by way of illustration and not limitation, diluents, fillers, agglutinants, disintegrants, disintegration inhibitors, absorption accelerators, adjuvant, binders, carriers, suspensing/dispersing agents, film formers/coatings, adhesives, antiadherents, wetting agents, lubricants, glidants, preservatives, sorbents, surface active agents, substances added to mask or counteract a disagreeable taste or odor, flavorings, colorants, fragrances, aromatising agents, sweeteners and substances added to improve appearance of the composition. The choice of excipient will to a large extent depend on factors such as the particular mode of administration, the effect of the excipient on solubility and stability, and the nature of the dosage form.

The pharmaceutical compositions of the present invention can be administered by a variety of routes including oral, parenteral, intravenous, subcutaneous, intramuscular, transmucosal (including buccal, sublingual, transurethral and rectal), topical, transdermal, by inhalation, permucous or percutaneous or using any other route of administration.

The polymorph φ of Fexofenadine hydrochloride can be administered in a variety of dosage forms, e.g., orally, in the form of tablets, sugar or film coated tablets, capsules, cachets, as a powder or granules; as a syrups, emulsions, solution or a suspension in an aqueous or non-aqueous liquid, as an oil-in-water liquid emulsion or a water-in-oil liquid emulsion, as a bolus, electuary or paste; rectally, in the form of suppositories; parenterally, e.g., intramuscularly, or through intravenous injection or infusion. The above described components for pharmaceutical composition administered are merely representative. Further materials as well as processing techniques and the like are set out in Part 5 of Remington's Pharmaceutical Sciences, 20$^{th}$ Edition, 2000, Merck Publishing Company, Easton, Pa., which is incorporated herein by reference. The compound of this invention can also be administered in sustained release forms or from sustained release drug delivery systems. A description of representative sustained release materials can also be found in the incorporated materials in Remington's Pharmaceutical Sciences. The pharmaceutical compositions containing the compound of the invention are usually prepared following conventional methods and are administered in a suitable pharmaceutical form.

In another embodiment, the invention provides the method of using the polymorph φ of Fexofenadine hydrochloride, comprising administering an effective amount of the polymorph to a patient in need thereof.

In another embodiment, the invention provides the use of compounds of formula (II) and (V) to prepare Fexofenadine hydrochloride.

While the present invention has been described in terms of its specific embodiments, certain modifications and equivalents will be apparent to those skilled in the art and are included within the scope of the present invention.

In the following, the present invention shall be illustrated by means of some examples, which are not construed to be viewed as limiting the scope of the invention.

EXAMPLES

XRPD analysis was performed on a APD 2000 Ital Structures diffractometer at room temperature, using a CuKα tube (40 kV, 30 mA) as the X-ray source. Data collection was made in 2θ step scan mode, at a scan speed of 0.02°/s in the range of 3° to 40° in 2θ.

DSC thermal analysis was performed on a Perkin Elmer Pyris 1 differential scanning calorimeter (5.7 mg, scan 30-250° C., 10° C./min).

DRIFT analysis was performed on a Perkin Elmer, Spectrum-One.

HPLC is the acronym for High Pressure Liquid Chromatography.

Example 1

Methyl 2-(4-(4-(4-(hydroxydiphenylmethyl)piperidin-1-yl)but-1-ynyl)phenyl)-2-methyl propionate oxalate (II)

In a 2 L four-neck flask equipped with mechanical stirrer, a thermometer and condenser, isopropanol (1 L) and methyl 2-(4-(4-(4-(hydroxydiphenylmethyl)piperidin-1-yl)but-1-ynyl)phenyl)-2-methylpropionate (82.4 g, 166 mmol) were added. The solution was heated to reflux under vigorous stirring. The solution was cooled to 40° C. and oxalic acid (15 g, 167 mol) was added. The solution was cooled to room temperature and stirred for 4 hours, to crystallize the oxalate salt. The solid was filtered, washed with isopropanol (200 mL) and dried under vacuum at 40° C., to give 94.4 g of (II), as a white solid. Yield: 94%.

Example 2

Methyl 2-(4-(4-(4-(hydroxydiphenylmethyl)piperidin-1-yl)but-1-ynyl)phenyl)-2-methyl propionate (III)

In a 5 L four-neck flask equipped with mechanical stirrer, a thermometer, a condenser and a dropping funnel, toluene (2 L), water (1 L) and methyl 2-(4-(4-(4-(hydroxydiphenylmethyl)piperidin-1-yl)but-1-ynyl)phenyl)-2-methylpropionate oxalate (II) (403 g, 688 mmol) were added. Under stirring, a water solution of ammonia (24%, 100 g, 1410 mmol) was added until pH 9 was reached. The phases were separated, the organic phase was washed with water (500 mL) and concentrated under vacuum to obtain 340 g of (III). Yield: 99.7%.

Example 3

2-(4-(4-(4-(Hydroxydiphenylmethyl)piperidin-1-yl)butanoil)phenyl)-2-methylpropanoic acid (V)

Methyl 2-(4-(4-(4-(hydroxydiphenylmethyl)piperidin-1-yl)but-1-ynyl)phenyl)-2-methyl propionate (III) (340 g) is dissolved in methanol (1790 mL). A solution of water (185 mL), sulfuric acid 98% (72 g, 722 mmol) and mercuric oxide (4.1 g, 19 mmol) was dropped: the temperature was maintained at about 40° C. The reaction was stirred for 8-10 hours and monitored by HPLC. At the end of the reaction, the mixture was dropped to a solution of sodium hydroxide (130 g, 3250 mmol) in methanol (650 ml) and water (200 mL). At reflux temperature, acetic acid (115 g, 1920 mmol) was added. The suspension was then cooled to 25-30° C. The solid was filtered under vacuum and washed with methanol (2×100 mL). The humid solid recovered was suspended in water (950 mL) and heated to 60-65° C. for about 1 hour. The solid was filtered and washed with hot water (2×100 mL), water at room temperature (2×100 mL) and finally with methanol (2×100 mL). About 311 g of the desired compound (V) still wet were obtained.

In a 2 L four-neck flask equipped with mechanical stirrer, a thermometer and a condenser, sodium hydroxide (23.6 g, 590 mmol) was added to the above obtained compound (V) (311 g) in methanol (850 mL). The mixture was heated to reflux to obtain a clear solution. Coal (12 g) was added and the mixture was heated to 40-45° C. for 15 minutes. The mixture was filtered on a Celite pad and the solid was washed with methanol (2×60 mL). The solution was reflux and acetic acid (41 g) was added. At the end of the addition, a solid precipitates. The suspension was cooled to 20-25° C., filtered under vacuum and the solid was washed with methanol (2×100 mL). 278 g of wet compound (V) were obtained, as a white solid, which was used for the next step without purification.

Example 4

2-(4-(1-Hydroxy-4-(4-(hydroxydiphenylmethyl)piperidin-1-yl)butyl)phenyl)-2-methylpropanoic acid (VI)

In a 2 L four-neck flask equipped with mechanical stirrer, a thermometer and a condenser, sodium hydroxide (22.6 g, 567 mmol) was added to 2-(4-(4-(4-(hydroxydiphenylmethyl)pi-piperidin-1-yl)butanoil)phenyl)-2-methylpropanoic acid (V) (278 g), in methanol (765 mL) and water (350 mL). The mixture was heated to 38-40° C. until complete dissolution of the solid, and a solution of sodium borohydride (9.8 g, 259 mmol), water (47 mL) and sodium hydroxide (100 mg) was dropped. The reaction mixture was stirred at 38-40° C. for about 4 hours and monitored by HPLC. The suspension was filtered and the solid was washed with a mixture of 1:1 water/methanol (2×80 mL), cooled to −10° C. and finally washed with water (2×100 mL). The solid was dried under vacuum at 40° C. to give 265 g of Fexofenadine free base (VI), as a white solid.

Example 5

Polymorph φ of Fexofenadine Hydrochloride

In a 500 mL four-neck flask equipped with mechanical agitator, a thermometer and a condenser, a suspension of 2-(4-(1-hydroxy-4-(4-(hydroxydiphenylmethyl)piperidin-1-yl)butyl)phenyl)-2-methylpropanoic acid (VI) (9 g, 17.9 mmol) in ethyl acetate (90 mL) was heated to 40° C. Then 30.36% aqueous hydrochloric acid (2 g, 20 mmol) was dropped to the mixture and the final solution was stirred at 40° C. for 1 hour and at room temperature overnight. The crystallized solid was filtered, washed with ethyl acetate and dried under vacuum at 50° C., to give 8.5 g of polymorph φ of Fexofenadine hydrochloride, as a white solid. Yield: 88%.

The invention claimed is:

1. A crystalline form φ of Fexofenadine hydrochloride having a water content comprised between 3.2 and 3.4%±0.1%; having an XRPD with peaks at 4.9, 9.9, 13.6, 15.8, 16.7, 18.1, 18.6, 19.9±0.2° 2θ and a DSC in accordance with FIG. 2.

2. The crystalline form φ according to claim 1, characterized by an XRPD in accordance with FIG. 1.

3. A process for producing the crystalline form φ of Fexofenadine hydrochloride according to claim 1, which comprises salifying a compound of formula (VI)

(VI)

with hydrochloric acid in an ester as a solvent
wherein said compound of Formula (VI) is prepared by
 a) hydrolyzing the oxalic acid of a compound of formula (II), (II)

wherein R is a $C_1$-$C_6$ alkyl, in presence of a base, to give a compound of formula (III)

(III)

wherein R is as defined above;

b) hydrating a compound of formula (III) in acid and optionally in the presence of a catalyst, to give a compound of formula (IV)

(IV)

wherein R is as defined above;

c) hydrolyzing a compound of formula (IV) to give a compound of formula (V)

(V)

and d) reducing a ketone of formula (V) into the hydroxy compound of formula (VI) with a reducing agent.

4. Process according to claim 3, wherein the base is potassium carbonate or ammonia.

5. Process according to claim 3, wherein the acid is hydrochloric acid or sulfuric acid; and the catalyst is mercury oxide.

6. Process according to claim 3, wherein the steps b) and c) are a "one pot" step.

7. Process according to claim 3, wherein the reducing agent is hydride or borohydride.

8. Process according to claim 3, wherein the temperature is 40° C.

9. Process according to claim 3, wherein the acid is sulphuric acid; and the catalyst is mercury oxide.

10. Process according to claim 3, wherein the reducing agent is borohydride.

11. Process according to claim 3, wherein the reducing agent is sodium borohydride.

12. The crystalline form φ according to claim 1, wherein the crystalline form φ is not hygroscopic.

13. A pharmaceutical composition comprising the crystalline form φ of Fexofenadine hydrochloride according to claim 1.

* * * * *